US005489670A

United States Patent [19]
Currie et al.

[11] Patent Number: 5,489,670
[45] Date of Patent: Feb. 6, 1996

[54] HUMAN UROGUANYLIN

[75] Inventors: Mark G. Currie, St. Charles; Toshihiro Kita, Creve Coeur; Kam F. Fok, St. Louis; Christine E. Smith, Manchester, all of Mo.

[73] Assignee: G. D. Searle & Co., Chicago, Ill.

[21] Appl. No.: 145,940

[22] Filed: Oct. 29, 1993

[51] Int. Cl.$^6$ .............................. A61K 38/00; C07K 5/00; C07K 7/00; C07K 4/00
[52] U.S. Cl. .............................................. 530/326
[58] Field of Search ............................... 530/326

[56] References Cited

U.S. PATENT DOCUMENTS 5,140,102  8/1992  Currie ........................ 530/36

OTHER PUBLICATIONS

Schulz et al., *Cell 63:* 941–948 (1985).
Yoshimura et al., *FEBS Lett. 181:* 138–142 (1985).
Currie et al., *Proc. Natl. Acad. Sci. 89:* 947–951 (1992).
de Sauvage et al., *Proc. Natl. Acad. Sci. 89:* 9089–9093 (1992).
Kuhn et al., *FEBS Lett. 318:* 205–209 (1993).
Wiegand et al., *FEBS Lett. 311:* 150–154 (1992).
Savarino et al., *Proc. Natl. Acad. Sci. 90:* 3093–3097 (1993).
Wiegand et al., *Biochem. Biophys. Res. Commun. 185:* 812–817 (1992).
Schulz et al., *J. Biol. Chem. 267:* 16019–16021 (1992).

*Primary Examiner*—Jill A. Warden
*Assistant Examiner*—Sheela J. Huff
*Attorney, Agent, or Firm*—Dennis A. Bennett

[57]  ABSTRACT

A novel peptide is disclosed which is useful for the control of intestinal fluid absorption and that has the following amino acid sequence

[SEQ ID NO: 1]

Asn—Asp—Asp—Cys—Glu—Leu—Cys—Val—Asn—Val—
1                        5                                     10

Ala—Cys—Thr—Gly—Cys—Leu
                           15

2 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asn  Asp  Asp  Cys  Glu  Leu  Cys  Val  Asn  Val  Ala  Cys  Thr  Gly  Cys  Leu
1                  5                          10                          15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Asp  Asp  Cys  Glu  Leu  Cys  Val  Asn  Val  Ala  Cys  Thr  Gly  Cys  Leu
1             5                         10                          15
```

HUMAN UROGUANYLIN

BACKGROUND OF THE INVENTION

This invention relates to a novel peptide and, more particularly, to a sedecapeptide that is an endogenous regulator of intestinal guanylate cyclase.

Guanylate cyclase is composed of a group of proteins that share structural characteristics relative to the enzymatic function of producing cyclic GMP, but differ quite remarkably in their selective activation by ligands. The three major forms of guanylate cyclase are the soluble, particulate, and intestinal (cytoskeletal-associated particulate or STa-sensitive) with each of these forms regulated by different ligands (1,2). Activation of the soluble guanylate cyclase occurs in response to nitric oxide (EDRF), while activation of the particulate enzyme occurs in response to the natriuretic peptides (atrial natriuretic peptide, brain natriuretic peptide, and C-type natriuretic peptide) (1,2). An endogenous activator of the intestinal guanylate cyclase only recently been identified. The first known endogenous activator was termed guanylin (3). However, the heat stable enterotoxin from E. coli has been known to selectively activate this form of the enzyme (4,5). This form of the enzyme is predominantly found in the intestinal epithelial cells with the largest number of receptors oriented towards the lumen (1,2). Recently, the intestinal form of guanylate cyclase has been cloned and expressed from rat small intestinal mucosa (6). This enzyme is characterized by an extracellular receptor binding region, a transmembrane region, an intracellular protein kinase-like region and a cyclase catalytic domain (6).

Pathogenic strains of E. coli and other bacteria produce a family of heat stable entertoxins (STs) that activate intestinal guanylate cyclase. STs are acidic peptides 18–19 amino acids in length with six cysteines and three disulfide bridges that are required for full expression of bioactivity (7). The increase of intestinal epithelial cyclic GMP elicited by STs is thought to cause a decrease in water and sodium absorbtion and an increase in chloride secretion (8,9). These changes in intestinal fluid and electrolyte transport then act to cause secretory diarrhea. In developing countries, the diarrhea due to STs is the cause of many deaths, particularly in the infant population (10). STs are also considered to be a major cause of traveler's diarrhea in developed countries (11). STs have also been reported to be a leading cause of morbidity in domestic animals (12).

BRIEF DESCRIPTION OF THE INVENTION

In accordance with the present invention a novel peptide is provided which has the following amino acid sequence. (NDDCELCVNVACTGCL)

[SEQ ID NO: 1]
Asn—Asp—Asp—Cys—Glu—Leu—Cys—Val—Asn—Val—
1           5                              10

Ala—Cys—Thr—Gly—Cys—Leu
                    15

This peptide, also referred to herein as human uroguanylin, has been isolated from human urine and has been chemically synthesized by solid phase peptide synthesis. In its oxidized active biologic form, the novel peptide has two disulfide bridges, one between cysteine residues at positions 4 and 12 and the other between cysteine residues at positions 7 and 15.

The peptide of this invention has been both isolated and chemically synthesized in a homogeneously purified form which did not exist in human urine from which it was initially obtained. That is, it has been prepared in a form which is essentially free of other low molecular weight peptides, and free from higher molecular weight material and other cellular components and tissue matter. This novel peptide has physiological characteristics which suggest that it is important to medical science in the study of regulators of guanylate cyclase. In particular, the novel peptide of this invention is an endogenous stimulator of intestinal guanylate cyclase. It has been found to stimulate increases in cyclic GMP levels in a manner similar to guanylin and the STs. As such regulator, it is useful for the control of intestinal absorption. It has potential to regulate fluid and electrolyte transport. Human uroguanylin also has been found to displace heat stable enterotoxin binding to cultured T84 human colon carcinoma cells. This cell line is known to selectively respond to the toxin in a very sensitive manner with an increase in intracellular cyclic GMP.

Human uroguanylin has been further demonstrated to act in an isolated intestinal rat preparation to stimulate an increase in short circuit current. This action is believed to be the physiologic driving force for eliciting chloride secretion and ultimately decreased water absorption. The human uroguanylin may thus act as a laxative and be useful in patients suffering from constipation, e.g. cystic fibrosis patients who suffer with severe intestinal complications from constipation.

BRIEF DESCRIPTION OF THE DRAWINGS

While the specification concludes with claims particularly pointing out and specifically claiming the subject matter regarded as forming the present invention, it is believed that the invention will be better understood from the following detailed description of preferred embodiments taken in conjunction with the accompanying drawings in which:

FIG. 3(a) Concentration-response effect of synthetic human uroguanylin, human guanylin and E. coli $ST_{5-18}$ (STa) on cyclic GMP levels in T84 cells. The cells were incubated with various concentrations of ligands for 30 min. Values represent mean±SE (n=4).

DETAILED DESCRIPTION OF THE INVENTION

Figure 1:
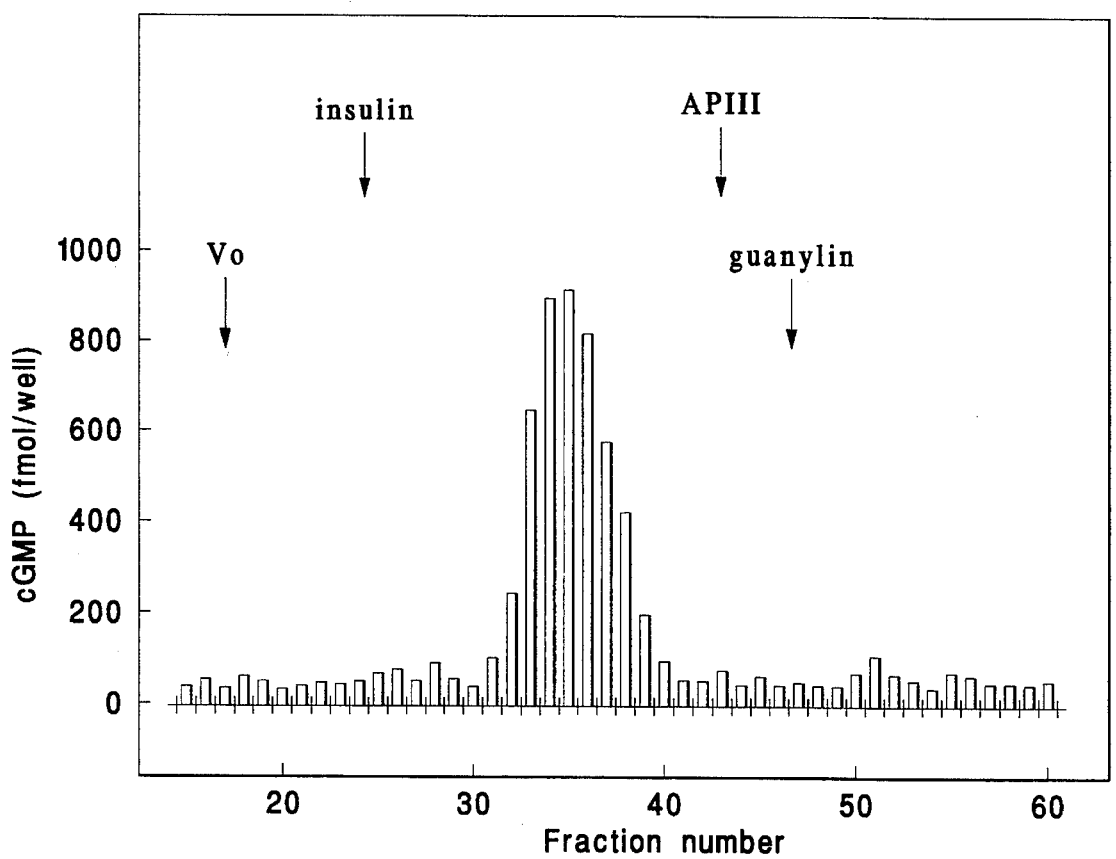
FIG. 1. Purification of uroguanylin from human urine by gel filtration chromatography. The extract of 5 liters of human urine was applied to 2.6×94 cm sephadex G-25 (superfine) gel filtration column. Isocratic 50 mM ammonium acetate was used to elute peptides at a rate of 0.5 ml/min and 5 ml of fractions were collected after 100 ml of initial elution. Molecular weight standards were separately assessed (Vo: blue dextran 200, insulin (MW 5750), atriopeptin III (AP III, MW 2550), rat guanylin (MW 1516)). All fractions were assessed in T84 cell cyclic GMP accumulation bioassay.

The novel peptide of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g. the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, arid reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

The acyl group on the N-terminus is conveniently introduced by reaction of an alkanoic anhydride with the peptide on the solid support after deprotection with TFA.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology*, 32, pp. 221–296, F. P. Nold, Ed., Interscience Publishers, New York, 1969; and Erickson and Merrifield, *The Proteins*, 1 Vol. 2, p. 255 et seq. (ed. Neurath and Hill), Academic Press, New York, 1976.

All references, patents or applications. U.S. or foreign, cited in the application are hereby incorporated by reference as if written herein.

In order to further illustrate the invention, the following exemplary laboratory preparative work was carried out. However, it will be appreciated that the invention is not limited to these examples or the details described therein.

EXAMPLE 1

Materials and Methods

Cell Culture. A cultured human colon carcinoma cell line (T84) was obtained from the American Type Culture Collection (Rockville, Maryland) (ATCC No. CCL 248) at passage 52. Cells were grown to confluency in 24-well culture plates with a 1:1 mixture of Ham's F12 medium and Dulbecco's modified Eagle's medium (DMEM), supplemented with 10% fetal calf serum, 100 IU/ml penicillin, and 100 μg/ml streptomycin. Cells were used at passages 54–60.

Cyclic GMP determination. Monolayers of T84 cells in 24-well plates were washed twice with 1 ml/well DMEM, then incubated at 37° C. for 10 min with 0.5 ml DMEM containing 1 mM isobutylmethylxanthine, a phosphodiesterase inhibitor. Agents and fractions were then added for the indicated time as described in the results section, below. The media was then aspirated and the reaction terminated by the addition of ice cold 0.5 ml of 0.1N HCl. Aliquots were then evaporated to dryness under nitrogen and then resuspended in 5 mM sodium acetate buffer, pH 6.4. The samples were then measured for cyclic GMP by conventional RIA as described by Steiner et al. (13).

Purification of Uroquanylin. Five separate batches of adult male human urine samples, 5 liters each, were collected and immediately placed on ice. The urine samples were applied to $C_{18}$ Sap-Yak columns (Waters). The columns were washed with 10% acetonitrile/0.1% trifluoroacetic acid (TFA)/$H_2O$ and eluted with 40% acetonitrile/0.1% TFA/$H_2O$. The eluted peptide fraction was lyophilized and resuspended in 7 ml of distilled $H_2O$ and centrifuged at 20,000×g for 20 min at 4° C. The resulting supernatant was separated by gel filtration chromatography (Sephadex G-25, superfine, 2.6×94 cm). The fractions were bioassayed and the active fraction was lyophilized. The sample was resuspended in 1 ml of 10% acetonitrile/0.1% TFA/$H_2O$ and applied to a $C_{18}$ semipreparative HPLC column (Vydac, Hasparia, Calif.). The column was developed with the following linear gradient: 10% acetonitrile/0.1% TFA/$H_2O$ to 40% acetonitrile/0.1% TFA/$H_2O$ in 120 min at a flow rate of 3 ml/min. The active fraction was lyophilized and resuspended in 1 m! of 10% acetonitrile/0.1% TFA/H20. The sample was applied to a a $C_{18}$ analytical HPLC column (Vydac) and active peptides were eluted using the above gradient over 180 min at a flow rate of 1 ml/min. Two active fractions were separately lyophilized and reconstituted in 0.05 ml of 0.1% TFA/$H_2O$. The samples were then separately applied to a $C_8$ microbore column (Applied Biosystems, Foster City, Calif.), eluted with an increasing gradient of 0.323% acetonitrile/min in 0.1% TFA/$H_2O$. Two separately purified peptides of each batch were then subjected to sequence analyses.

N-Terminal Protein Sequence Analysis. Automated Edman degradation chemistry was used to determine the N-terminal protein sequence. An applied Biosystems, Model 470A gas-phase sequencer was employed for the degradations (14) using the standard sequencer cycle, 03RPTH. The respective phenylthiohydantoin (PTH)-amino acid derivatives were identified by reverse-phase HPLC analysis in an on-line fashion employing an Applied Biosystems, Model 120A PTH Analyzer fitted with a Brownlee PTH-$C_{18}$ column. Reduction and pyridylethylation for cysteine residue identification was performed directly on the filter (15).

Electrospray Mass Spectrometry. The molecular weights of uroguanylin samples were determined by a previously described technique (3,16). Briefly, a triple quadrupole mass spectrometer equipped with an atmospheric pressure ion source was used to sample positive ions produced from an electrospray interface. Mass analysis of sample ions was accomplished by scanning the first quadrupole in 1 atomic mass unit increments from 1000 to 2400 atomic mass units in ≈3 s and passing mass-selected ions through the second and third quadrupoles operated in the rf-only mode to the multiplier. For maximum sensitivity, the mass resolution of the quadrupole mass analyzer was set so that ion signals were ≈2 atomic mass units wide at half peak height, but the centroid of the ion signal, still represented the correct mass of the ion.

Radioligand Binding Assay. $^{125}$I-labeled $ST_{5-18}$ ($^{125}$I-ST) was prepared by the Iodo-Gen method as previously described (3). T84 cell monolayers were washed two times with 1.0 ml per well of ice-cold binding assay buffer (Earle's medium containing 25 mM 2[N-Morpholino] ethanesulfonic acid (MES), pH 5.5). The cells were incubated for 30 min at 37° C. in 0.5 ml per well of binding assay buffer with $^{125}$I-ST (100,000 cpm per well) and unlabeled peptides. Then the cells were washed four times with 1 ml of ice-cold binding assay buffer and solubilized with 0.5 ml of 1M NaOH per well. This volume was transferred to tubes and assayed for radioactivity by a multigamma counter. Results are expressed as the percentage specifically bound.

Measurement of Short-Circuit Current (ISc) in Rat Colon. Rat proximal colon tissue, consisting of only mucosa and submucosa, was mounted between two Ussing half-chambers and bathed on both sides similar to previously reported (3). Electrical measurements were monitored with an automatic voltage clamp, and direct connecting voltage-and current-passing electrodes were used to measure trans epithelial potential difference and Isc. Tissues were equilibrated under short-circuit conditions until Isc had stabilized.

Chemical Synthesis of Uroquanylin. Uroguanylin was synthesized by the solid-phase method (17,18) on an Applied Biosystems Model 430A peptide synthesizer and purified by reverse-phase $C_{18}$ chromatography. The purity and the structure were verified by analytical HPLC, amino acid composition analysis, mass spectroscopy, and sequence analysis.

RESULTS

Figure 2:
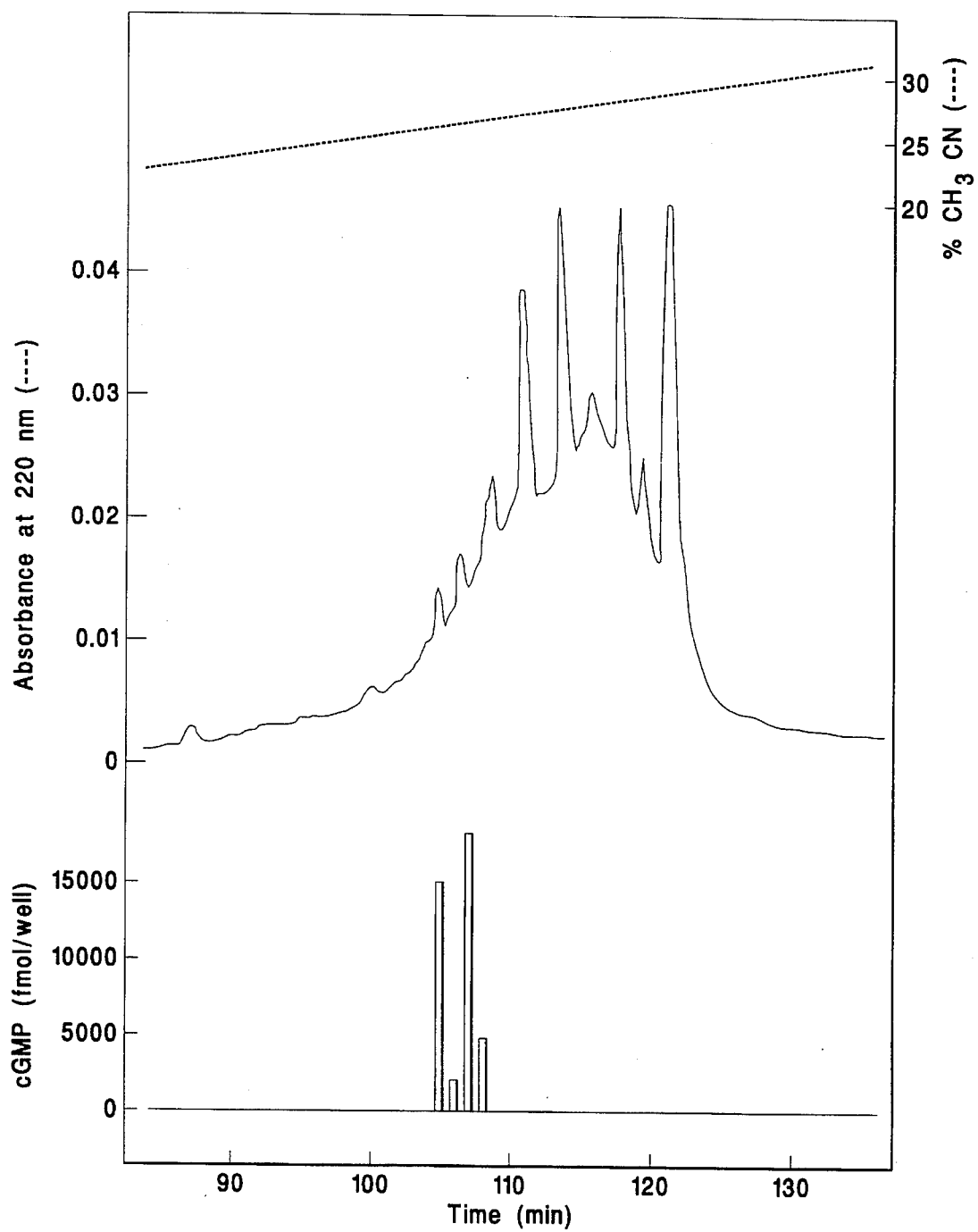
FIG. 2. Purification of uroguanylin from human urine by reverse-phase HPLC. Five liters of human urine extract was purified through the semipreparative reverse-phase HPLC and active fraction was fractionated on an analytical $C_{18}$ column (Vydac). A linear gradient of 10% to 40% acetonitorile, 0.1% TFA was developed at 1.0 ml/min over 3 hrs. One min fractions were collected and assayed for activity in T84 cell cyclic GMP bioassay. This figure shows the biological active region with two peaks associated with changes in UV absorbance.
Figure 3A:
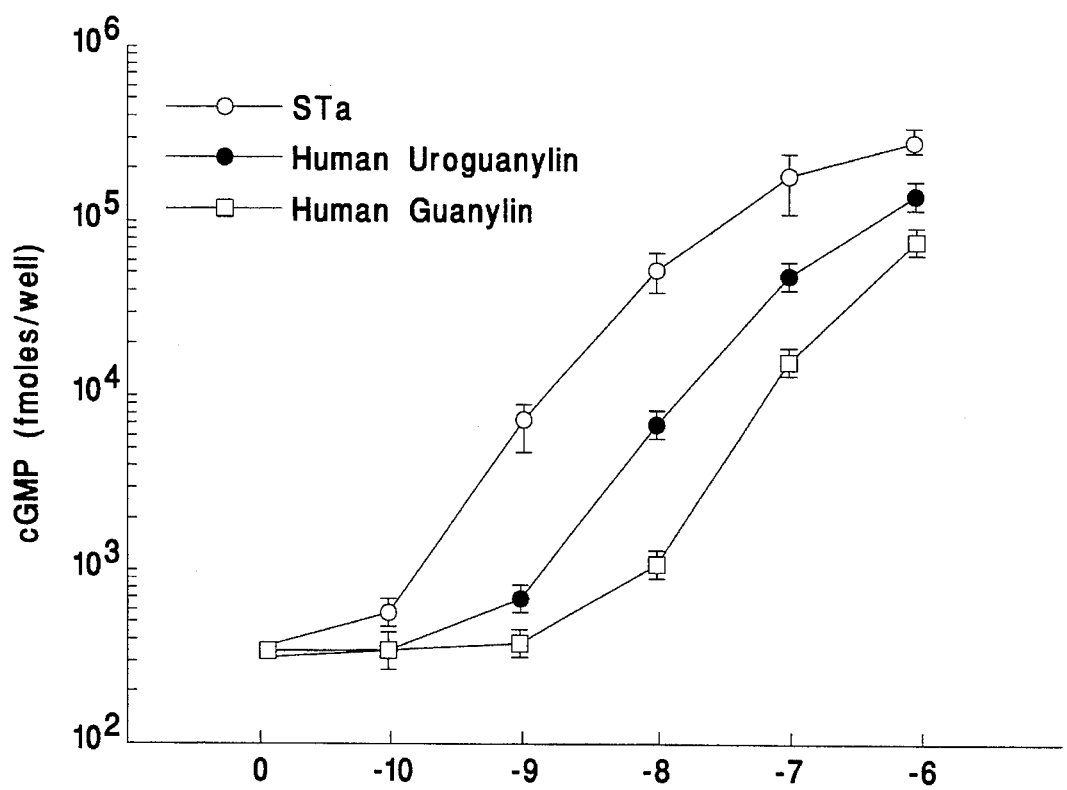
FIG. 3(a) and (b).
Figure 3B:
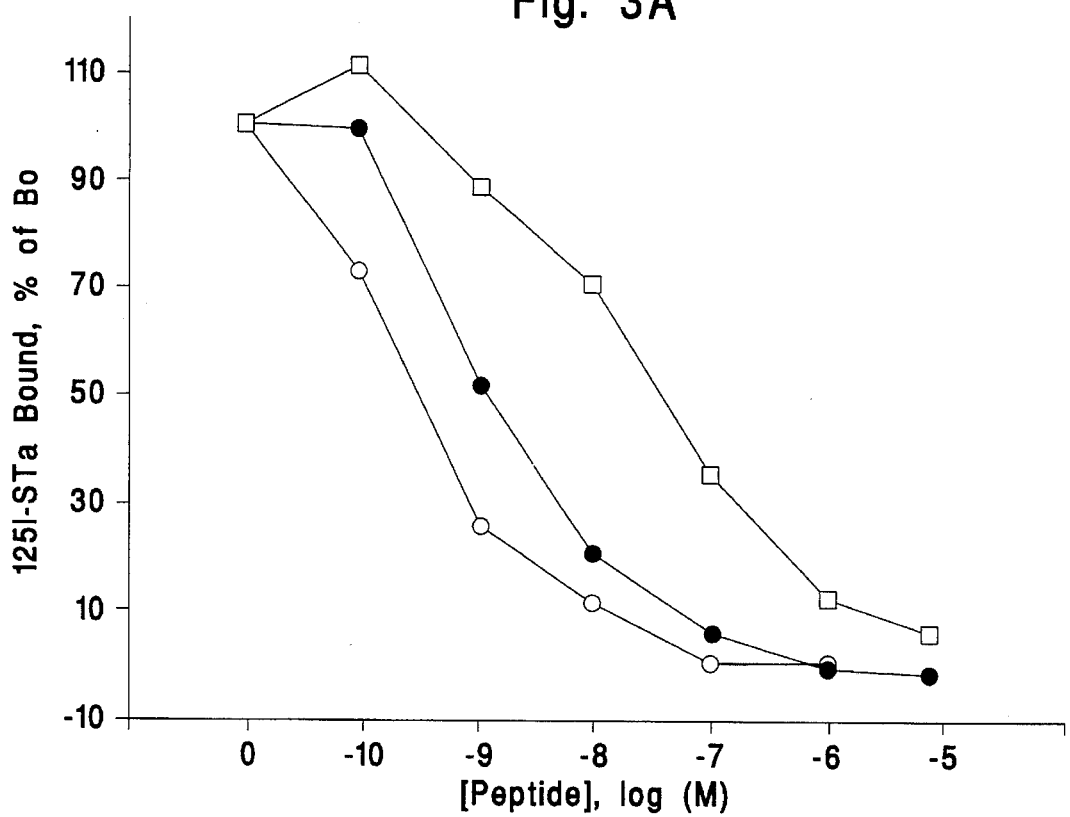
FIG. 3(b) Displacement of $^{125}$I-STa specific binding from T84 cells by human uroguanylin, human guanylin and STa. Cells were incubated for 30 min at 37° C. with labeled STa and indicated concentrations of ligands. Specific binding (%) was determined by dividing the specifically bound $^{125}$I-STa at each ligand concentration by the specifically bound $^{125}$I-STa in the absence of ligands. Each determination represents the mean of four wells examined.

In initial experiments, the peptide fraction of human urine samples resulting from $C_{18}$ Sep-Pak extraction was assayed for activity to increase cyclic GMP levels in T84 cells. These preliminary experiments strongly suggested the presence of guanylate cyclase stimulatory activity. The urine extract was subjected to fractionation by gel-filtration and a series of reverse-phase HPLC steps in order to produce a sufficiently pure preparation for the purpose of structural determination. Fractionation by G-25 gel filtration chromatography yielded a single major bioactive fraction that migrated on the column with an apparent size of 5,000 daltons (FIG. 1). Subsequently, this active fraction was further purified by reverse-phase HPLC using a semipreparative $C_{18}$ column and the bioactivity was determined to reside in only one fraction eluting at 27.8% acetonitrile/0.1% TPA/$H_2O$ (data not shown). Further purification by reverse-phase HPLC using a $C_{18}$ analytical column yielded two active fractions that appeared to elute with peaks of substances that absorbed at 220 nm (FIG. 2). These two fractions were separately subjected to further characterization by microbore HPLC ($C_8$ column) and each fraction exhibited a single bioactive peak that absorbed at 220 nm (data not shown). The amino acid sequences of the two peaks were independently determined by the Edman degradation procedure. The sequences are NDDCELCVNVACTGCL [SEQ ID NO:1] and DDCELCVNVACTGCL [SEQ ID NO:2], respectively for peaks 1 and 2. These two peptides are identical except that the peptide contained in peak one possesses an additional amino acid (asparagine) at the N-terminus. It is likely that peak two is a degradation product of peak 1, probably a result of aminopeptidase action. Electrospray mass spectrometric analysis of the two fractions yielded observed molecular weights of 1666.6 and 1552.6 atomic mass units, respectively for the peptides contained in peaks 1 and 2, respectively. These molecular weights correspond to the theoretical molecular weights derived from the sequences if two disulfide bonds link the four cysteines, and therefore indicate that the full sequences of these peptides were determined by N-terminal protein sequence analysis.

Comparison of the sequence of peak 1 with other proteins in the GenBank, National Biomedical Research Foundation, and SwissProt databases by computer-based search indicates that this sequence is a unique sequence. This search did reveal that human uroguanylin shares homology with guanylin and ST. Thus, human uroguanylin appears to be a member of the guanylin/ST family of peptides.

Chemical synthesis of bioactive human uroguanylin (the sedecapeptide) was accomplished by directed folding of the peptide. The synthetic bioactive peptide possesses disulfide-linked bridges between the 4–12 and 7–15 amino acid positions. Analysis of the biological activity of human uroguanylin was assessed by determining its effect on T84 cyclic GHP levels, competition binding studies with $^{125}$I-ST as the radioligand in T84 cells, and stimulation of Cl-secretion as reflected by increases in Isc rat colon.

Figure 4:
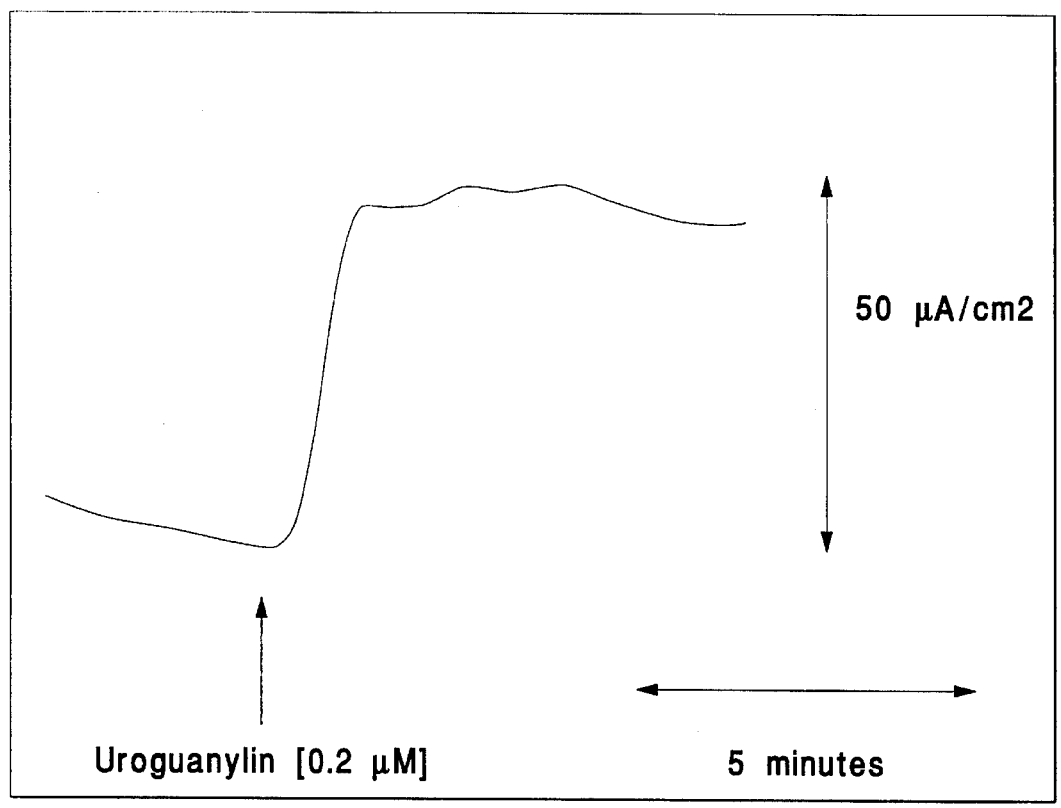
FIG. 4. Effect of synthetic human uroguanylin on short-circuit current (Isc) of rat colon. Effect of human uroguanylin (0.2 μM) on Isc across rat proximal colon after a mucosal addition. The response is characteristic of results from 3 other experiments.

Synthetic human uroguanylin caused a concentration-dependent increase in T84 cell cyclic GMP (FIG. 4a). Human uroguanylin appeared to be more potent than human guanylin, but less potent than ST for activation of GC-C in T84 cells. A different profile of relative affinity was obtained using the competitive binding assay with $^{125}$I-ST$_{5-18}$ as the radioligand. ST and human uroguanylin had similar affinities for the receptors on T84 cells and human guanylin had a much lower affinity (FIG. 4b). The data indicate that these peptides all possess the ability to stimulate GC-C and share similar binding sites with varying degrees of relative affinities for the receptors in T84 cells.

To assess the effect of human uroguanylin on well characterized ST- and guanylin-sensitive transport functions, we assessed the effects of the peptide on Isc of proximal rat colon. In these experiments, the measurement of Isc is used as an indicator of transepithelial chloride secretion. Previous studies in these preparations have indicated that the charge in Isc elicited by ST and guanylin is mostly accounted for by an increase in chloride secretion. Human uroguanyglin added to the mucosal reservoir of rat colon mounted in an Ussing chamber also caused a sustained rise in Isc (FIG. 5).

Various other examples will be apparent to the person skilled in the art after reading the present disclosure without departing from the spirit and scope of the invention. It is intended that all such other examples be included within the scope of the appended claims.

REFERENCES

1. Singh, S. Lowe, K. G., Thorpe, D. S. Rodriquez, H., Kuang, W.-J., Dangott, L. J., Chinkers, H., Goeddel, D. B., and Garbers, D. L. {1988) *Nature* 334, 708–712.

2. Waldman, S. A., and Murad, F. (1987) *Pharmacological Reviews* 39, 163–196.

3. Currie, H. G., Fok, K. F. , Karo, J., Moore, R. J., Hamra, F. K. Duffin, K. L., and Smith, C. E. {1992) *Proc. Natl. Acad. Sci. USA* 89,947–951.

4. Field, H., Graf, L. H., Laird, W. J., and Smith, P. L. (1978) *Proc. Natl Acad. Sci. USA* 75, 2800–2804.

5. Guerrant, R. L., Hughes, J. M., Chang, B., Robertson, D.C., and Hurad, F. (1980) *J. Infect Dis.* 142, 220–228.

6. Schulz, S., Green, C. K., Yuen, P. S. T., and Garbers, D. L. (1990) *Cell* 63,941–948.

7. Yoshimura, S., Ikemura, H., Watanabe, H., Aimoto, S., Shimonishi, Y., Hara, S., Takeda, T., Miwatani, T., and Takeda, Y. (1985) *FEBS Letters* 181, 138–142.

8. Field, H., Rao, C. H., and Chang, E.B. (1980) *New England J. Med.* 321, 879–883.

9. Guarino, A., Cohen, M., Thompson, M., Dharmsathaphorn, K., and Giannella, R. (1987) *Am. J. Physiol.* 253, G775–G 780.

10. Robins-Browne, R. M. (1987) *Rev. Infect. Dis.* 4, 28–53.

11. Levine, M. M. (1987) *J. Infect. Dis,* 155, 377–389.

12. Burgess, M. N., Bywater, R. J., Cowley, C. M., Mullan, N. A., and Newsome, D. M. *Infect. Immun.* 21, 526–531.

13. Steiner, A. L., Paghara, A. S., Chase, L. R., and Kipnis, D. M. (1972) *J. Biol. Chem.* 247, 1114–1120.

14. Hunkapiller, M. W., Hewick, R. M., Dreyer, R. J., and Hood, L. E. (1983) *Methods Enzymol,* 91, 399–413.

15. Kruft, V., Ulrike, K., and Wittmann-Liebold, B. (1991) *Anal. Biochem.* 193, 306–309.

16. Bruins, A. P., Covey, T. R., Henion, J. D. (1987) *Anal. Chem.* 59, 2642–2651.

17. Merrifield, R. B. (1963) *J. Am, Chem. Soc.* 85, 2149–2154.

18. Tam, J. P., Wu, C.-R., Liu, W., and Zhang, J.-W. (1991) *Twelfth American Peptide Symposium,* Abstract LW5.

---

What is claimed is:

1. A purified peptide having the following amino acid sequence

[SEQ ID NO: 1]
Asn—Asp—Asp—Cys—Glu—Leu—Cys—Val—Asn—Val—
1          5                   10

Ala—Cys—Thr—Gly—Cys—Leu
               15

2. The peptide of claim 1 in oxidized form having two disulfide bridges, one between cysteine residues 4 and 12 and the other between cysteine residues 7 and 15.

* * * * *